(12) United States Patent
Michaelson (10) Patent No.: US 7,621,742 B2
(45) Date of Patent: Nov. 24, 2009

(54) ORTHODONTIC HAND TOOL SYSTEM (76) Inventor: Dennis J. Michaelson, 1570 Satterfield, Pocatello, ID (US) 83201

( * ) Notice: Subject to any disclaimer, the term of this patent is extended or adjusted under 35 U.S.C. 154(b) by 286 days.

(21) Appl. No.: 11/116,938

(22) Filed: Apr. 27, 2005

(65) Prior Publication Data
US 2005/0255421 A1 Nov. 17, 2005

Related U.S. Application Data (60) Provisional application No. 60/567,285, filed on Apr. 30, 2004.

(51) Int. Cl.
A61C 3/00 (2006.01)
(52) U.S. Cl. ............... 433/4; 433/156; 606/210; 81/419; 294/99.2
(58) Field of Classification Search .......... 433/3, 433/4, 153, 156, 159; 606/210; 294/99.2; 81/418, 419, 420, 427; D24/143; D28/55
See application file for complete search history.

(56) References Cited

U.S. PATENT DOCUMENTS

| 1,033,942 | A | * | 7/1912 | Ruggles | 294/99.2 |
|---|---|---|---|---|---|
| 1,174,004 | A | * | 2/1916 | Greenwald | 294/99.2 |
| 1,386,436 | A | * | 8/1921 | Smith | 294/99.2 |
| 2,665,692 | A | * | 1/1954 | L'Esperance | 606/148 |
| 3,489,151 | A | * | 1/1970 | Eller | 606/106 |
| 4,610,252 | A | * | 9/1986 | Catalano | 606/157 |
| 4,976,718 | A | * | 12/1990 | Daniell | 606/131 |
| 5,007,827 | A | * | 4/1991 | DiFranco | 433/4 |
| 5,147,369 | A | * | 9/1992 | Wagner | 606/107 |
| D406,409 | S | * | 3/1999 | Rubino | D29/127 |
| D406,734 | S | * | 3/1999 | Doherty et al. | D7/686 |
| 6,776,615 | B2 | * | 8/2004 | Dietrich | 433/159 |
| 6,840,768 | B1 | * | 1/2005 | Rabal | 433/159 |
| D530,994 | S | * | 10/2006 | Jarvis et al. | D7/686 |
| 7,458,622 | B2 | * | 12/2008 | Tardif et al. | 294/16 |
| 2008/0179903 | A1 | * | 7/2008 | Tardif et al. | 294/16 |

* cited by examiner

Primary Examiner—Ralph A Lewis (57) ABSTRACT

A system of tools for use in an orthodontic setting made up of a series of individual tools. Each tool comprises a pair of flat, generally elongated arms placed in an adjacent lengthwise relationship and connected at each first ends in a manner so as to force the remaining portions of the arms apart. Each of the tools has specially modified features that allow the tools to perform specific functions such as: scraping teeth and orthodontic devices; grasping orthodontic brackets; placing orthodontic brackets onto a tooth without disturbing other free-floating brackets; measuring the distance between portions of a tooth so as to ensure proper bracket placement; measuring the distance between orthodontic brackets; and aseptically retrieving objects from a drawer.

11 Claims, 10 Drawing Sheets

ORTHODONTIC HAND TOOL SYSTEM

CLAIM TO PRIORITY

This application is a non-provisional application which claims the priority date from the provisional application entitled ORTHODONTIC HAND TOOL SYSTEM filed by Dr. Dennis J. Michaelson on Apr. 30, 2004 with application Ser. No. 60/567,285, the disclosure of which is incorporated herein by reference.

BACKGROUND OF THE INVENTION

1. Field of the Invention

The present invention generally relates to orthodontic hand tools, and more particularly to tools used in procedures commonly performed in dentists and orthodontists offices.

2. Background Information

In the fields of orthodontics and dentistry, a variety of hand tools are commonly used to perform procedures within a patient's mouth. These hand tools include tools to probe, measure and hold various pieces of both mouth tissue as well as orthodontic hardware. These tools assist the practitioner in grasping, holding, moving and replacing various items within a patient's mouth.

One of the most common procedures performed by an orthodontist involves the placing and positioning of corrective devices commonly called braces. The typical arrangement for braces requires placement of a series of brackets upon a patient's teeth. Most brackets have a base portion that is affixed to a patient's tooth surface and a wing portion, which extends away from the base and forms a channel into which a connecting wire is placed. A connecting wire is placed between the channels of the braces and applies pressure upon the teeth so as to straighten the teeth and achieve a desired result.

The placement of the brackets upon a patient's teeth requires that alignment and positioning of the brackets be obtained before the brackets are bonded into place. Usually, the brackets are placed upon a patient's tooth in a free-floating alignment. After the brackets have been oriented to the desired position and orientation on the teeth, the brackets are bonded to the teeth of the patient using a fixing means such as a light source or ultrasonic waves.

One way of placing the brackets is to use a pair of long handled curved tweezers to grasp a portion of the bracket and to place the back portion of the bracket onto adhesive glue that has been pre-applied to the enamel of the teeth. One problem that occurs with most of these types of tweezers is that the beaks of the tweezers extend too far from the curve portion of the tweezers. Thus, while attempting to place a bracket against a tooth, the angled portion of the tweezers contacts an adjacent bracket that had already been placed and aligned. This contact often forces the prior placed and aligned bracket out of alignment and requires subsequent resetting of the formerly aligned bracket. As a result, the process of placing and aligning brackets can be long and tenuous, as aligned brackets are constantly disrupted by the placement of an adjacent bracket. This constant resetting significantly impairs and slows the process of placing braces.

In addition to these problems, the placement of brackets upon a tooth can be awkward or difficult for the person placing the brackets. The rear teeth (called the "sevens") are particularly difficult to place brackets on or work on because these teeth are located to the rear of the mouth and the orthodontist must work in a limited space encumbered by the patient's teeth, tongue, gums, and cheek. Traditionally configured pliers cannot reach back into these spaces and, as a result, placement of orthodontic brackets in these locations can be exceedingly difficult, cumbersome, and time consuming.

After the brackets are aligned in a desired location and orientation, the adhesive is then bonded or sealed onto the tooth by the use of a light or other means. The placement of the bracket onto the enamel causes excess glue to be displaced onto the surface of the tooth. If this adhesive is not removed, an unsightly glue spot can result. In addition, the presence of the adhesive on a tooth can serve as a trap for plaque and cause tooth decay. The shape and dimensions of most prior art tweezers make removing or scraping this adhesive away difficult or impossible because the thickness of the beaks is too large to allow such scraping. Furthermore, thick prior art tweezers do not allow placement of a bracket by grasping the bracket within the wire engaging groove.

An additional problem that occurs in placing brackets upon a patient's tooth is the inaccurate placement of the brackets in a desired spacing or location. Bracket placement upon a tooth is critical to efficient orthodontics. The height of the bracket on the tooth is especially important. Each type of tooth may have a different ideal bracket placement height. For example, canines require a different bracket than incisors. Often orthodontists utilize different separate devices to check height, while some simply "eyeball" the location.

Measuring the location for placement of a bracket requires measuring distances within the mouth with a very small measuring device. By contacting the patient, this measuring device becomes contaminated. Orthodontists also use rulers to measure the distance between brackets and to determine what size coil spring to place. A ruler is also used to measure and determine how much overbite the patient has on each appointment. This allows the orthodontist to track a patient's progress.

Most orthodontists use plastic rulers. These plastic rulers have a variety of disadvantages. First, plastic rulers cannot be heat sterilized. Therefore, they must either be disposed of, which increases costs, or treated with a germicide in order to sterilize them for use in other patients' mouths. This cold sterilization process requires that plastic rulers be soaked in a cold sterilizing solution for several minutes. Some parties may be impatient and not wait the designated time; thus sterility is not achieved. If the designated time is allowed to elapse, the ruler must still be placed back in the drawer or on a separate tray setup. This individual handling requires more effort to maintain organization. Parties may forget to sterilize the rulers or may place them in different locations. As a result, a sterile ruler is often difficult to find when needed. This often causes the orthodontist or dentist to wait while a ruler is found. This waiting is inefficient and costly to the orthodontist.

An additional problem that exists in dental or orthodontic practices is that an individual, while working in a patient's mouth, will need to retrieve supplies from a closed drawer. Usually, this individual will be wearing gloves. If something is needed from a nearby drawer, the drawer cannot be opened with their gloves because these gloves have been contaminated by contact with the patient. If the drawer is opened and an object retrieved by a party with contaminated gloves, all of the objects that come into contact with the glove will then also become contaminated.

One solution to this problem is to remove the contaminated gloves, retrieve the object from the drawer, and put on new gloves. This procedure is not efficient or wholly sanitary, as hands may become contaminated by contact with a soiled glove. Furthermore, if another object needs to be retrieved from the drawer, this entire process must then be repeated. This is cumbersome and expensive. In some cases, such precautions are simply not undertaken. A party will simply open the drawer with the contaminated hand and retrieve the item that they need. This action is unsanitary and unacceptable.

Another solution in this situation is to open the drawers with a contaminated glove and then wipe down the drawer handle with a germicide. This procedure, however, has several problems. First, the wiping action may miss small areas, leaving an area for bacteria and other germs to proliferate. Second, an employee may simply forget or neglect wiping the drawer handles. Third, in order for the germicide to function properly and sterilize the surface of the handle, a period of time must elapse. It is impractical to touch the drawer, apply the germicide, wait for the germicide to sterilize the drawer, and then open the drawer.

Therefore, what is needed is an aseptic way to easily access objects within a drawer of a dental or orthodontic office without contaminating objects of the drawer. What is also needed is a tool with appropriately dimensioned portions so as to provide grasping abilities for placing orthodontic brackets upon a patient's teeth. What is also needed is an orthodontic tool that will allow for placement of an orthodontic bracket in a free-floating arrangement without disturbing a proximate bracket. What is also needed is an orthodontic tool for engaging in a variety of activities connected with the orthodontic placement of a bracket. What is also needed is an accessible measuring device for measuring the placement of brackets upon a patient's teeth. What is also needed is a heat sterilizable ruler attached to a dental tool. What is also needed is a heat sterilizeable system of tools having the aforementioned capabilities.

Therefore, it is an object of this invention to provide a series of heat sterilizable dental tools with the ability to grab and place an orthodontic brace upon a tooth. It is a further object of the invention to provide an orthodontic tool that allows placement of a bracket on a tooth without disturbing a bracket on a proximate tooth. It is a further object of the invention to provide a tool for obtaining sterile access to drawers in a medical or dental office. Another object of the invention is to provide a sterilizeable, easily accessible tool for measuring distances within a patient's mouth. Another object of the invention is to provide a sterilizeable system of orthodontic tools that can perform a variety of functions in an orthodontic setting.

Additional objects, advantages and novel features of the invention will be set forth in part in the description as follows, and in part will become apparent to those skilled in the art upon examination of the following, or may be learned by practice of the invention. The objects and advantages of the present invention may be realized and obtained by means of the instrumentalities and combinations particularly pointed out in the appended claims.

SUMMARY OF THE INVENTION

A system of tools for use in an orthodontic setting is made up of a series of individual tools. Each tool comprises a pair of flat, generally elongated arms placed in an adjacent lengthwise relationship and connected at each first end in a manner so as to force the remaining portions of the arms apart.

A first tool is made up of a pair of flat, generally elongated arms, placed in an adjacent lengthwise relationship. Each arm has a shape wherein a first end extends to a central portion. The central portion then extends to a tapered portion. i.e., a tapered member. The tapered portion extends to a first curved portion connected to a tapered beak, forming an acute angle adjacent to the arms. The beak has an inner surface and an outer surface and is dimensioned so as to allow the beak to grasp an orthodontic bracket below its wings, near its base or within the wire channel. The outer surface of the beak is also inscribed with markings to designate the distance between the tip of the beak and a designated mark. These markings function to measure the distance from a point on a tooth to ensure proper placement of an orthodontic bracket.

A second measuring device extends from the first end to a hook for scraping material. This second measuring device is also inscribed with markings that designate distances between the markings and the distance from the end of the hook. This device allows an orthodontist to measure a variety of longer distances within the patient's mouth.

A second tool is made up of a pair of flat, generally elongated arms, placed in an adjacent lengthwise relationship. Each arm has a shape wherein a first end extends to a central portion. The central portion then extends to a tapered portion, i.e., a tapered member. The tapered portion extends to a first curved portion. The first curved portion extends to a second curved portion and forms an obtuse angle adjacent to the arms. The second curved portion then extends at an acute angle to a tapered beak at the second end. The beak has an inner surface and an outer surface and is dimensioned so as to allow the tool to grasp a base portion of an orthodontic bracket behind the wings or near its base and place the bracket on a tooth.

A third tool is made up of a pair of flat, generally elongated arms, placed in an adjacent lengthwise relationship. Each arm has a shape wherein a first end extends to a central portion. The central portion then extends to a tapered portion. i.e., a tapered member. The tapered portion extends to a first curved portion connected to a tapered beak forming an acute angle adjacent to the arms. The beak has an inner surface and an outer surface. Connected to the inner surface of each beak is a semicircular plate dimensioned to allow grasping of the bracket under its wings, near its base, and within the wire channel. The plates are also designed to function as a tool for scraping material from the teeth of a patient. The semicircular plates also enable the orthodontist to maintain a better grasping angle upon the tool while being able to access the desired areas of the patient's mouth from a variety of angles.

A fourth tool is made up of a pair of flat, generally elongated arms, placed in an adjacent lengthwise relationship. Each arm has a shape wherein a first end extends to a central portion. The central portion then extends to a tapered portion, i.e., a tapered member. The tapered portion extends to a first curved portion. The first curved portion extends to a second curved portion and forms an obtuse angle adjacent to the arms. The second curved portion then extends at an acute angle to a tapered beak at the second end. The beak has an inner surface and an outer surface. The inner surface of each beak has a semicircular plate dimensioned to allow grasping of the bracket, beneath its wings, near its base or within the wire channel and also allows the plate to function as a tool for scraping material from the teeth of a patient. These semicircular plates enable the orthodontist to maintain a better grasping angle upon the tool, while being able to access the desired areas of the patient's mouth.

A fifth tool is made up of a pair of flat generally elongated arms placed in an adjacent lengthwise relationship and connected at each first ends in a manner so as to force the remaining portions of the arms apart. These arms extend from said first end to a central portion, from said central portion to a notched portion, and from said notched portion to a curved portion extending to a beak. Each of the notched portions is semicircular and dimensioned so as to be able to grasp a wire type drawer handle. The notched portions are positioned so as to be generally perpendicular to an axis between the first end and the second ends of the arms. This tool allows a party to aseptically open a drawer and retrieve material therein.

A sixth tool is made up of a pair of tweezers with a shortened beak that extends from a curved anchor portion. The beak and end of the tweezers contain indicia, which mark distances from the end of tool. These measuring devices are very useful in determining the location, position, and orientation of items within a person's mouth and are of assistance in determining the proper placement of items upon a tooth surface.

In use, the tools of the invention allow the orthodontist to perform a variety of functions such as: scraping teeth and orthodontic devices; grasping orthodontic brackets; placing orthodontic brackets onto a tooth without disturbing other free-floating brackets; measuring the distance between portions of a tooth so as to ensure proper bracket placement; measuring the distance between orthodontic brackets; and aseptically retrieving objects from a drawer.

These tools also allow the orthodontist to access brackets and perform procedures within a patient's mouth while maintaining their hand in a more favorable and stronger position. Another advantage of one of the tools of the invention is that it allows sterile access to drawers within an orthodontist's office. Another advantage of the system of tools is that it provides for a set heat sterilizable tool capable of performing all of these functions that is not easily misplaced or lost.

Still other objects and advantages of the present invention will become readily apparent to those skilled in this art from the following detailed description wherein I have shown and described only the preferred embodiment of the invention, simply by way of illustration of the best mode contemplated by carrying out my invention. As will be realized, the invention is capable of modification in various obvious respects all without departing from the invention. Accordingly, the drawings and description of the preferred embodiment are to be regarded as illustrative in nature, and not as restrictive.

DESCRIPTION OF THE PREFERRED EMBODIMENTS

While the invention is susceptible of various modifications and alternative constructions, certain illustrated embodiments thereof have been shown in the drawings and will be described below in detail. It should be understood, however, that there is no intention to limit the invention to the specific form disclosed, but, on the contrary, the invention is to cover all modifications, alternative constructions, and equivalents falling within the spirit and scope of the invention as defined in the claims.

The present invention is a series of dental or orthodontic tools designed to perform a variety of functions. The system is comprised of a variety of tools having specialized characteristics and designed for working within a patient's mouth.

Figure 1:
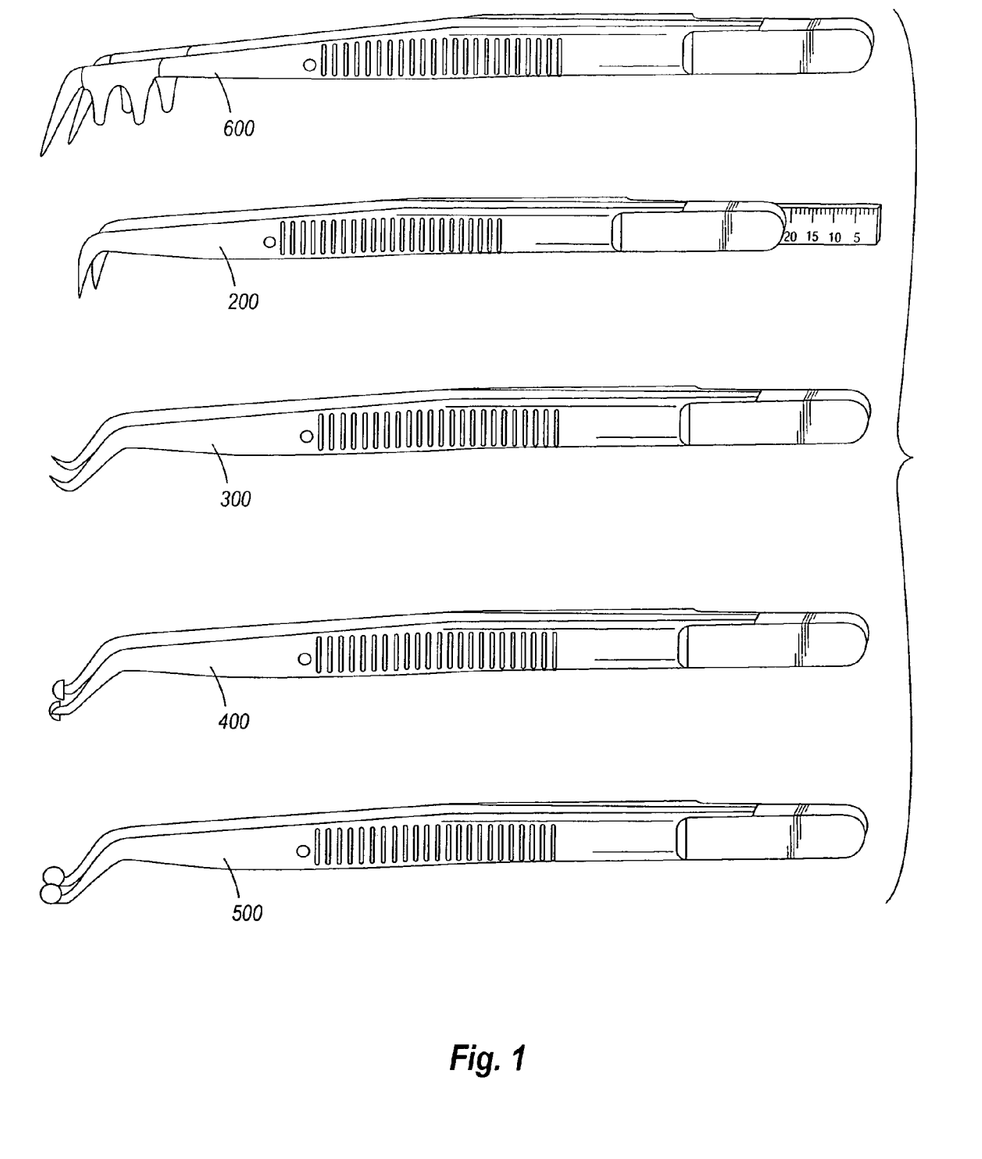
FIG. 1 is a top plan view of a first embodiment of the invention showing a series of individual tools.

Referring now to FIG. 1, a first embodiment of the tool system of the present invention is shown. In this embodiment, the outlay of the tools in the system, including a combination tools in the set, is shown. In a preferred embodiment of the invention, the tools would be marked, grouped, and used together as a set. This set could be sterilized together and would ensure that individual tools of the set were not misplaced. Other common tools could also be added to the set to provide the desired tools, depending upon the choice of the orthodontist or the dental user involved.

In a preferred embodiment, all of the tools of the system are made of a heat sterilizable material, such as stainless steel. However, other materials could also be used and are contemplated by this invention. In a preferred embodiment of the invention, all of the various tools of the system are kept together in a stainless steel cassette and sterilized as a unit. By keeping the individual tools together as a unit, the orthodontist knows where the tools are at all times.

Figure 2:
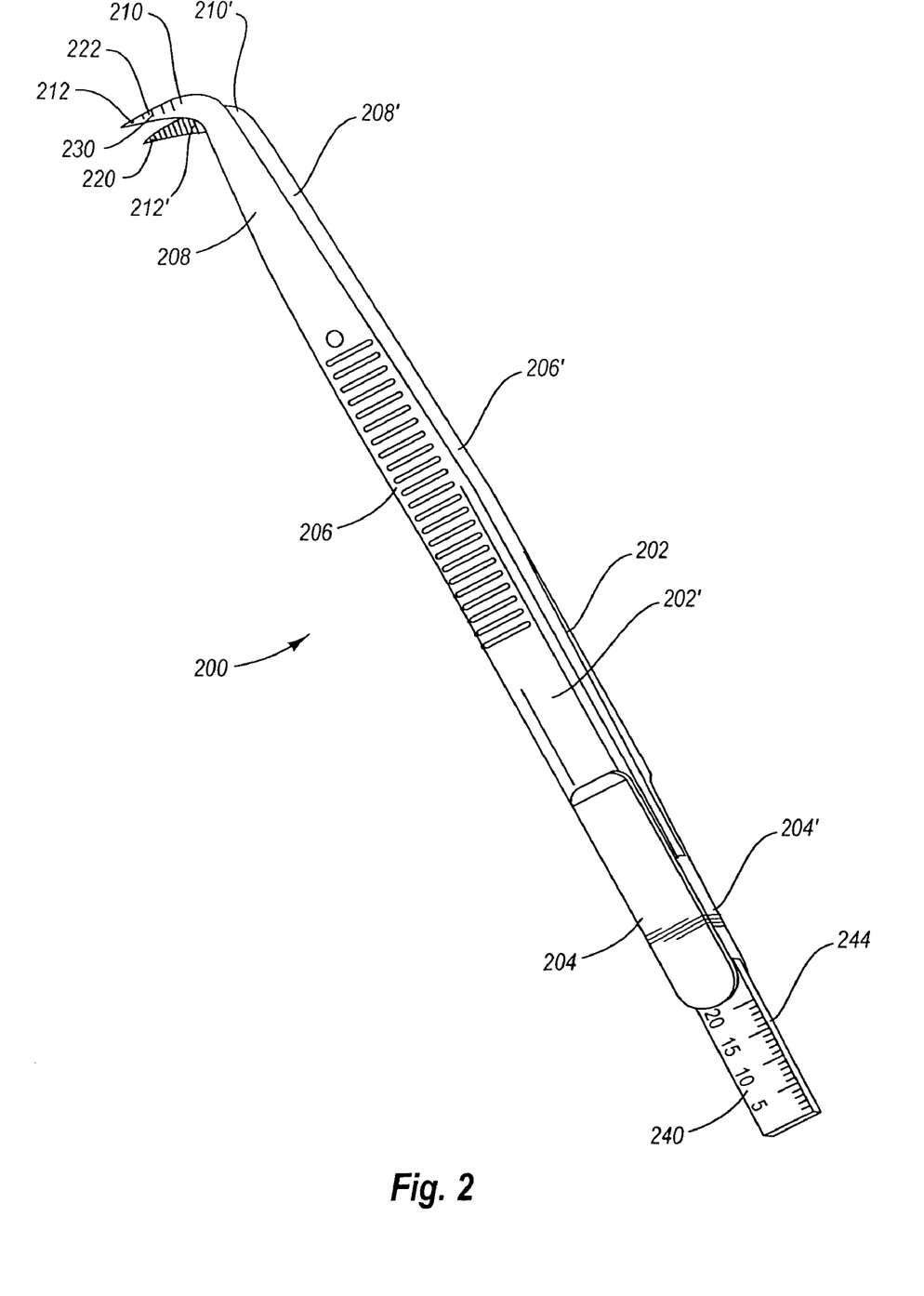
FIG. 2 is a detailed perspective view of a first tool of the system shown in FIG. 1.

Referring now to FIG. 2, a detailed view of a first tool 200 of the system 100 shown in FIG. 1 is shown. This tool 200 is an improvement over dental and orthodontic tools found in the prior art in that the dimensions and configuration of this tool 200 are adapted to grasp and place orthodontic brackets on teeth and to perform other delicate procedures in and around the teeth themselves.

This tool comprises a pair of flat, generally elongated arms 202, 202' positioned in a generally lengthwise relationship. Each arm 202, 202' has a first end 204, 204' and extends to a central portion 206, 206'. The central portions 206, 206' extend to a tapering portion, i.e., a tapering member 208, 208'. The tapering portions 208, 208' extend to curved portions 210, 210'. The curved portions 210, 210' extend to a second end of the arm and is formed like a beak 212, 212'. Each of the beaks 212, 212' have an inner surface 220 and an outer surface 222. The arms 202, 202' are connected at the first ends 204, 204' and are configured to maintain the central portions 206, 206', tapered portions 208, 208', curved portions 210, 210', and inner surface beak portions 220 apart. In a preferred embodiment, the dimensions of the arms 202, 202' are reduced so as to better fit within a user's hand.

The curved portions 210, 210' form an angle with regard to an axis formed between the first ends 204, 204' and the curved portions 210, 210'. This angle is a more acute angle than the angle on most prior art instruments and provides for greater ability in grasping items used in an orthodontic practice, such as orthodontic brackets. In addition, the thickness of the beaks 212, 212' taper as they extend away from the curved portion 210, 210' and are dimensioned so as to enable the tool to grasp and manipulate small objects. In particular, the beaks 212, 212' are dimensioned so as to allow an orthodontic bracket to be grasped in a variety of positions and locations, including below the wings of the bracket, near the base of the bracket, and within the wire channel of the bracket. These increased grasping capabilities, together with the dimensions of the tool, allows an individual using this tool be able to act more quickly and be more precise in placing the brackets upon a tooth. In addition, the small beaks 212, 212' also allow the person using the tool 200 to clean the excess glue from around the bracket and the tooth.

This tool 200 also has measuring markings 230 etched into the outer surface of the beak 220. In a preferred embodiment, these markings 230 are on a millimeter scale. However, other scales may also be used. These markings 230 eliminate the necessity of changing instruments from a hand tool to a bracket height gauge and then back to the hand tool for each bracket placement. While in this embodiment of the system the markings are placed on this particular tool 200, it is to be distinctly understood that these markings may be placed on any of the tools that are designed for placement within the mouth of the patient.

At the first ends 204, 204' of this version of the present invention is a ruler 240. Orthodontists use rulers to measure many things, including the distance between brackets to decide what size coil spring to place, to measure a patient's overbite, and measure a patient's progress towards a desired result. This ruler has a set of ruler markings 244. These markings may be in metric, English or other designated increments. The thickness of the ruler 240 is preferably less than eighteen one-thousandths of an inch. This allows the ruler 240 to be placed within the wire slot of a typical orthodontic bracket and to be used as an orientation device in the placement of orthodontic brackets. While in this embodiment of the system the ruler is located on this particular tool 200, it is to be distinctly understood that this ruler may be placed on any tool that is designed for placement within the mouth of the patient.

The dimensions and features of the present invention allow for use of the device to perform the delicate movements required to accurately place the orthodontic brackets to be done more easily and without the problem of adjacent bracket displacement as is found by the prior art devices. Having the ruler attached to one of the tools and made out of a heat sterilizeable material enables the ruler to prevent being lost and allows the ruler to be sterilized every time that the instruments are run through the heat sterilization cycle. By combining the tweezers and ruler, an instrument is eliminated. The ruler may also have a hook attached thereto as an additional scraping tool.

Figure 3:
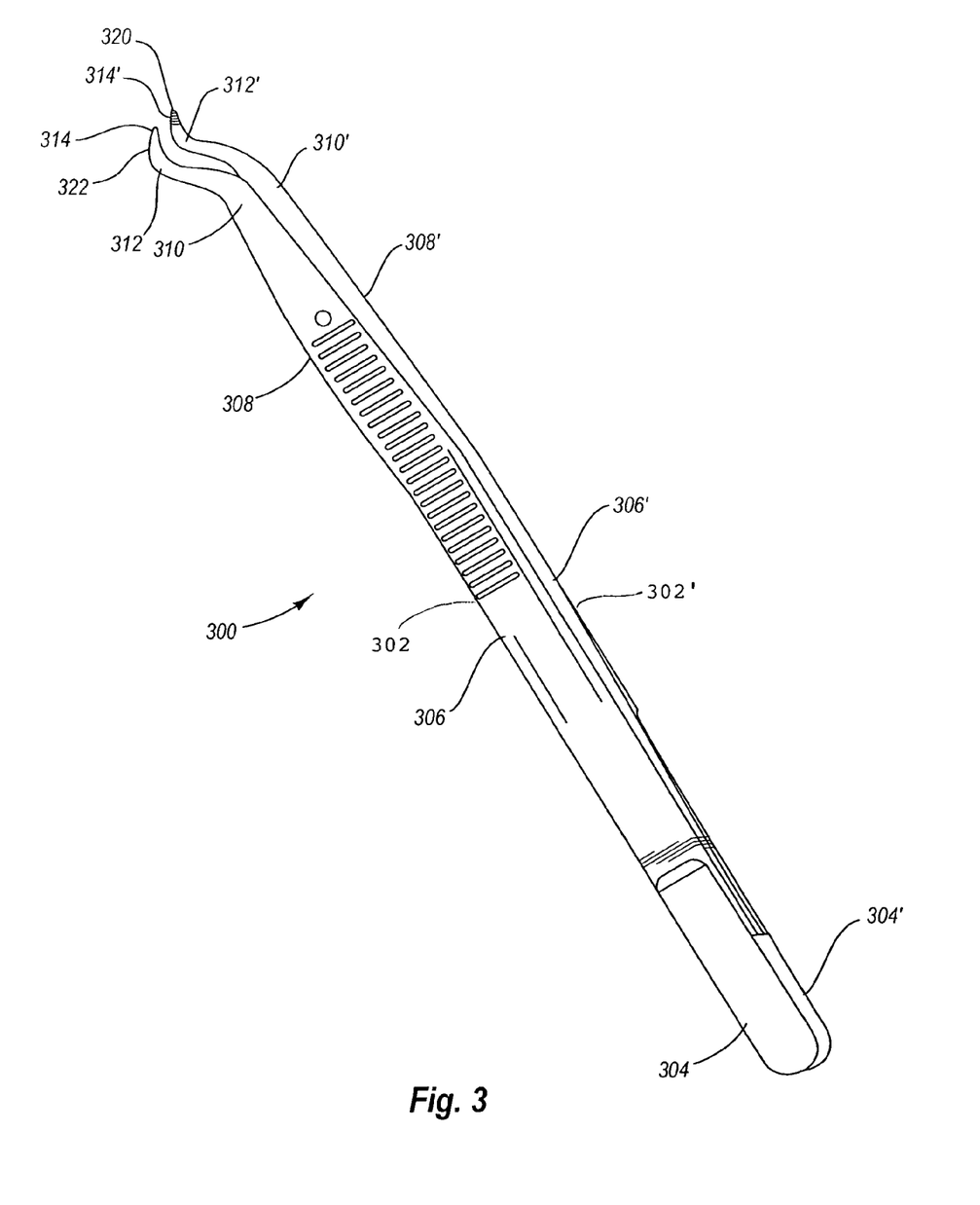
FIG. 3 is a detailed perspective view of a second tool of the system shown in FIG. 1.

Referring now to FIG. 3, we see an embodiment of a second tool 300 of the present invention. This tool embodiment incorporates the features of the first tool 200, but is specifically designed to allow placement of brackets on the rear teeth called molars, or "7's". This tool 300 is made up of up of a pair of flat, generally elongated arms 302, 302'. Each arm 302, 302' having a first end 304, 304' extending to a central portion 306, 306'. The central portion 306, 306' extend to a tapering portion, i.e., a tapering member 308, 308'. The tapering portion 308, 308' extends to first curved portions 310, 310', while the first curved portions 310, 310' extend in a direction obtuse to the first ends of the arms 304, 304'. The first curved portions 310, 310' extend to second curved portions 312, 312'. The second curved portions 312, 312' are directed in an orientation opposite the orientation of the first curved portions 310, 310'. The second curved portions 312, 312' extend to beaks 314, 314' at second ends 316, 316'. The beaks 314, 314' each have an inner surface 320 and an outer surface 322. The arms 302, 302' are connected at their first ends 304, 304' and are configured to keep the central portions 306, 306', tapered portions 308, 308', first curved portions 310, 310', second curved portions, 312, 312', and beak inner surfaces 320 apart. If so desired, the outer surface of the beaks 322 may be etched with markings so as to allow for measuring the brackets upon a tooth.

The dimensions of the second curved portions 312, 312' and the beak portions 314, 314' are tapered so as to allow a person using the tool the ability to grasp an orthodontic device such as a bracket within a wire slot, behind its wings or near its base. The first curved portions 310, 310' and second curved portions 312, 312' are configured to allow the person using the tool better access to the rear teeth of the patient's mouth.

Figure 4:
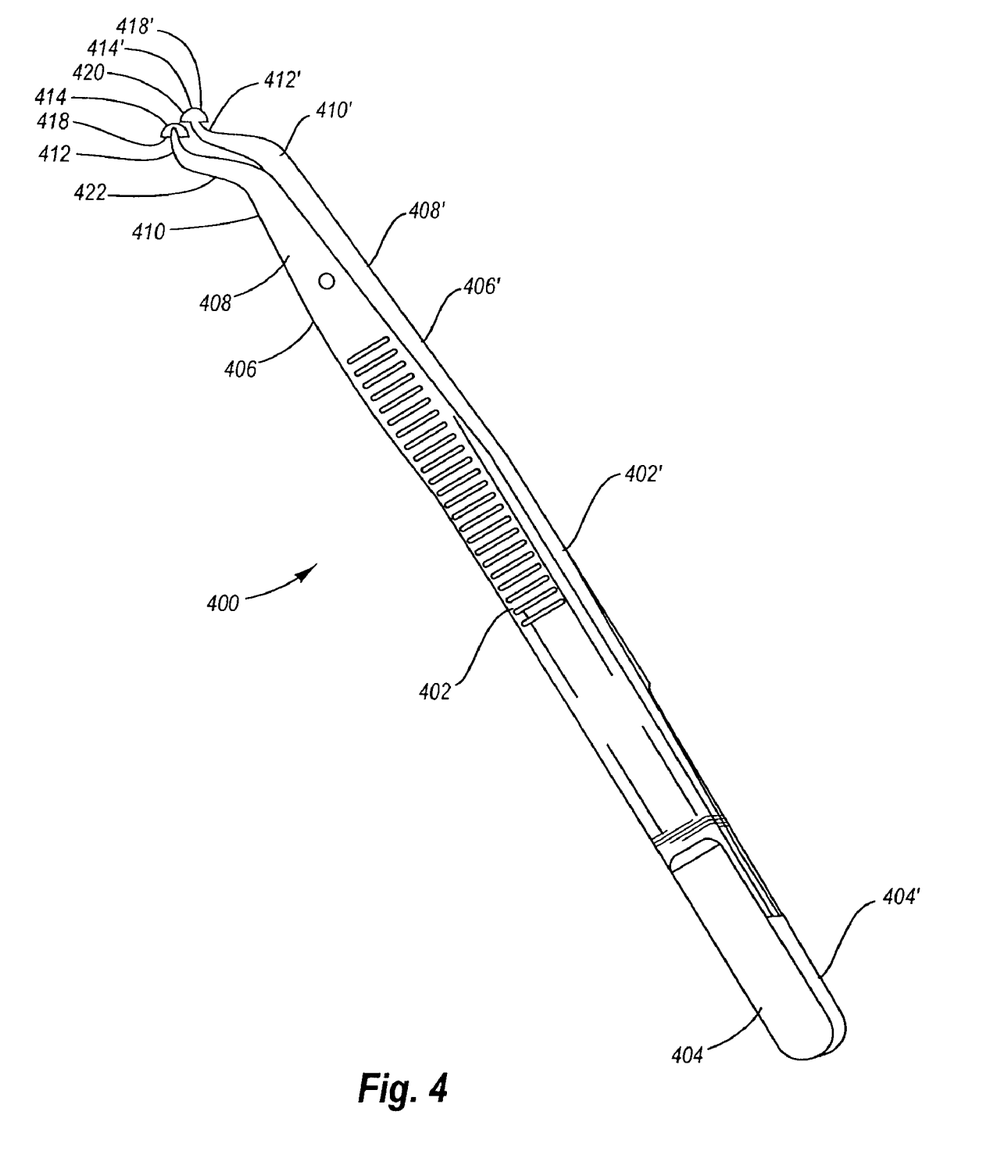
FIG. 4 is a detailed perspective view of a third tool of the system shown in FIG. 1.

Referring now to FIG. 4, a third tool 400 of the present invention is shown. This tool 400 comprises a pair of flat, generally elongated arms 402, 402' arranged in a generally lengthwise relationship. Each arm 402, 402' has a first end 404, 404' and extends to a central portion 406, 406'. The central portions 406, 406' extend to tapering portions, i.e., tapering members 408, 408'. The tapering portions 408, 408' extend to curved portions 410, 410'. The curved portions 410, 410' extend to beaks 412, 412' located at the second ends 414, 414' of the arm Each of the beaks 412, 412' have an inner surface 420 and an outer surface 422. The arms 402, 402' are connected at the first ends 404, 404' and are configured to keep the central portions 406, 406', tapered portions 408, 408', curved portions 410, 410', and inner surface beak portions 420 apart. Attached to each of the inner surface beak portions 420 are plates 418. Each of these plates 418 are dimensioned so as to allow access and grasping of an orthodontic bracket. In a preferred embodiment, the plates 418, 418' are semicircular or oval shaped, but any shape that would assist the user to perform its desired functions and features may be used.

The plates 418, 418' are adapted to grasp an orthodontic bracket. In some embodiments, the plates 418, 418' may also be adapted so they are able to be inserted into the slot of the bracket.

The dimensions of the plates 418, 418' are adapted to grasp an orthodontic bracket. In some embodiments, the plates 418, 418' may also be adapted so they are able to be inserted into the wire slot of the bracket.

Figure 5:
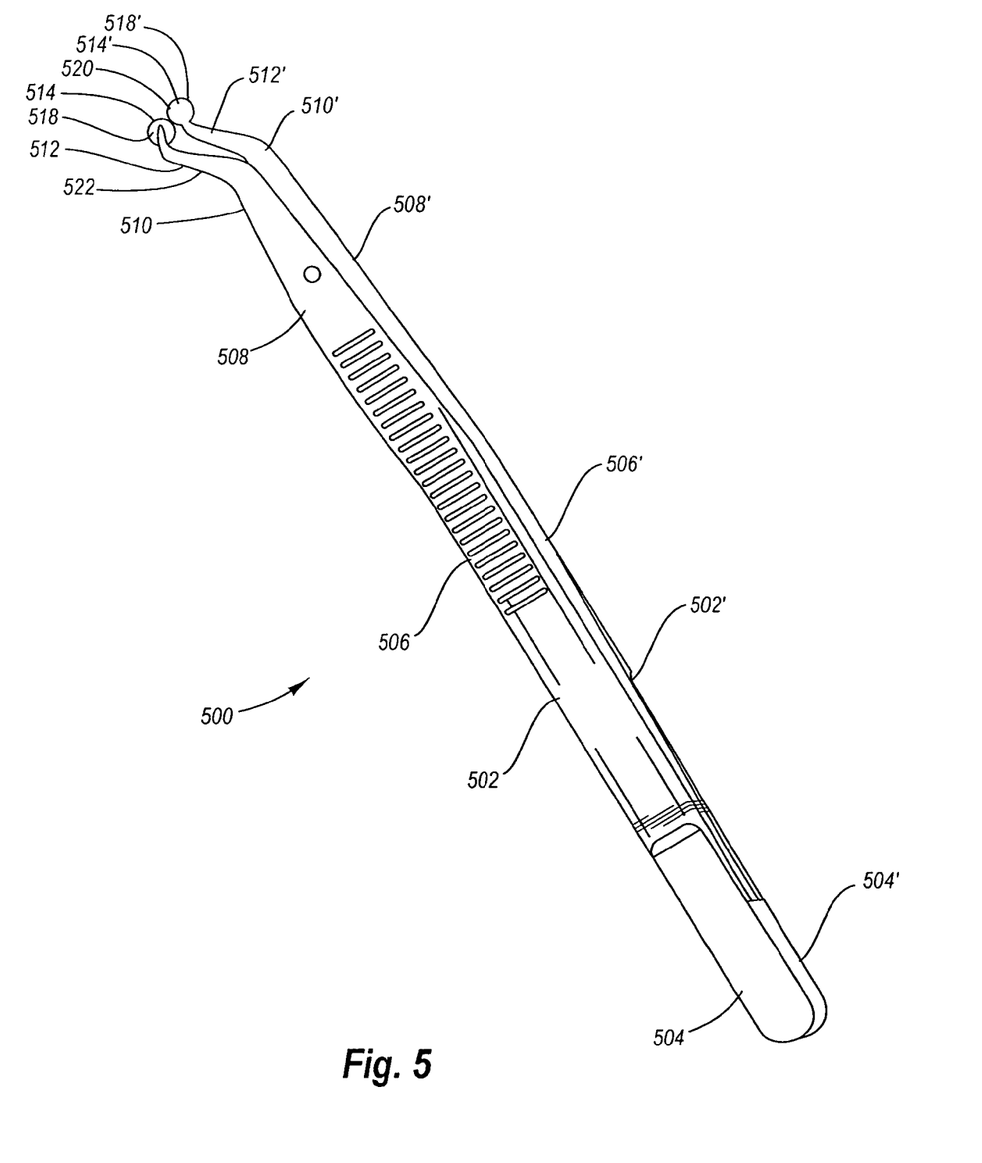
FIG. 5 is a detailed perspective view of a fourth tool of the system shown in FIG. 1.

Another tool of the present invention is found in FIG. 5. This tool 500 is made up of up of a pair of flat, generally elongated arms 502, 502'. Each arm 502, 502' having a first end 504, 504' extending to a central portion 506, 506'. The central portions 506, 506' extend to a tapering portion, i.e., a tapering member 508, 508'. The tapering portions 508, 508' extend to first curved portions 510, 510', while the first curved portions 510, 510' extend to second curved portions 512, 512'. The second curved portions 512, 512' are directed in an orientation opposite the orientation of the first curved portions 510, 510'. The second curved portions 512, 512' extend to second ends terminating in beaks 514, 514'. The beaks 514, 514' each have an inner surface 520 and an outer surface 522.

The arms 502, 502' are connected at their first ends 504, 504' and are configured to keep the central portions 506, 506', tapered portions 508, 508', first curved portions 510, 510', second curved portions, 512, 512', and beak inner surfaces 520 apart.

The angle and length added by the second curved portions 512, 512' allow for a person using the tool to obtain better access to the rear teeth of the patient's mouth. This access is further assisted by plates 518, 518' attached to the beak inner surfaces 520. Each of these plates 518, 518' are dimensioned so as to allow access and grasping of an orthodontic bracket. While in this embodiment the plates 518, 518' are generally circular or oval shaped, any shape that suits the needs of the orthodontist may be used.

These plates 518, 518' also allow orthodontists to use the tool while working all around the mouth of a patient without having to flex their wrist or change the position of their grip. The access to various portions of the mouth is increased by the presence of a second set of curves 512, 512'. This allows the orthodontists to maintain their hands in a stronger position and prevents the braces or brackets from slipping, flipping or being dropped. In this preferred embodiment the plates 518, 518' are semi-circular in shape but other shapes that provide these same advantages may also be used.

The plates 518, 518' are adapted to grasp the bottom portion of an orthodontic bracket. In some embodiments the plates 518, 518' may also be adapted so to be able to be inserted into the bracket wire slot of an orthodontic bracket.

Figure 6:
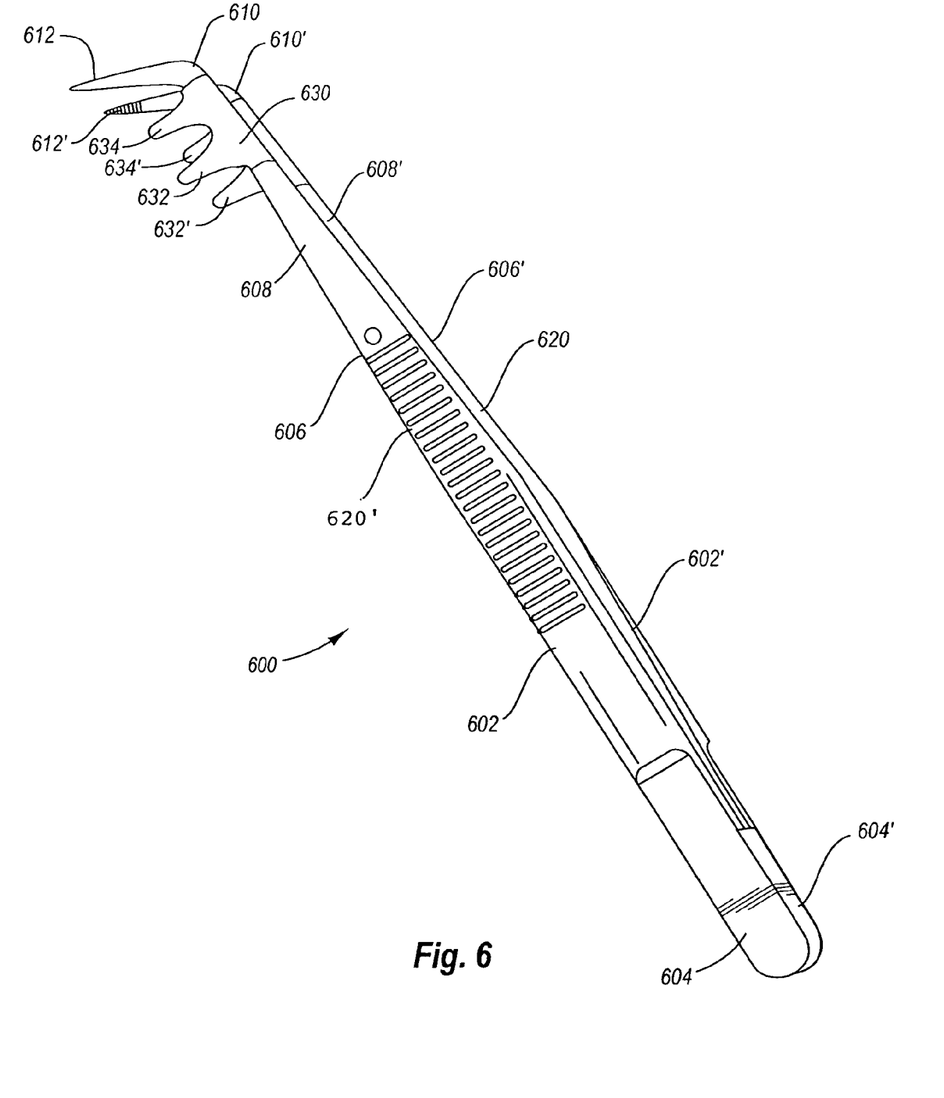
FIG. 6 is a detailed perspective view of a fifth tool of the system shown in FIG. 1.

Another tool of the present invention is shown in FIG. 6. This tool 600 is made up of a pair of flat, generally elongated arms 602, 602'. Each arm 602, 602' having a first end 604, 604' extending to a central portion 606. The central portion 606 extends to a tapering portion, i.e., a tapering member 608. The tapering portion 608 extends to a first curved portion 610. The first curved portion 610 extending to a second end terminating in a beak 612. The beaks having an inner surface 620 and an outer surface 622. The arms 602, 602' are connected at said first ends 604, 604' and are configured to keep said central portions 606, 606', tapered portions 608, 608', curved portions 610, 610', and said inner beak surfaces 620, 620' apart. These tweezers also include a drawer grasping portion 630. The first drawer grasping portion, i.e., first grasping finger 632, 632' extends from the tapering portion 608, 608' of said arm 602, 602' and extends in a curved fashion to a second portion, i.e., a second grasping finger 634, 634', The curved portion between the two drawer handle grasping portions 632, 632' are adapted so as to allow grasping of a wire type drawer handle. While in this embodiment of the invention the drawer grasping portions or fingers 632, 632' are configured and adapted so as to allow the device to grasp a wire type drawer handle, it should be understood that the invention is in no way limited thereto but must be variously embodied and configured so as to function with a variety of other types of drawer handles.

These drawer handle grasping portions or fingers 632 632' are adapted to fit around the typical drawer in a medical and/or dental facility which has a wire pull type handle. The drawer handle grasping portions or fingers 632, 632' not only allow a person to open the drawer with greater ease, but to also open and close the drawer without the beak portions 612, 612' or the fingers of the user coming into contact with the drawer handle. Once the grasping portions have been used to open the drawer, the beak portions 612, 612' may be used to retrieve objects out of the interior of the drawer. Thus, the contents of the drawer remain uncontaminated. The drawer grasping portions of this tool 632, 632' are distinctive and will prevent the use of this tool in a patient's mouth. Nevertheless, this tool may also be placed into a sterilization container and sterilized along with the other tools and materials shown in FIG. 1.

Figure 7:
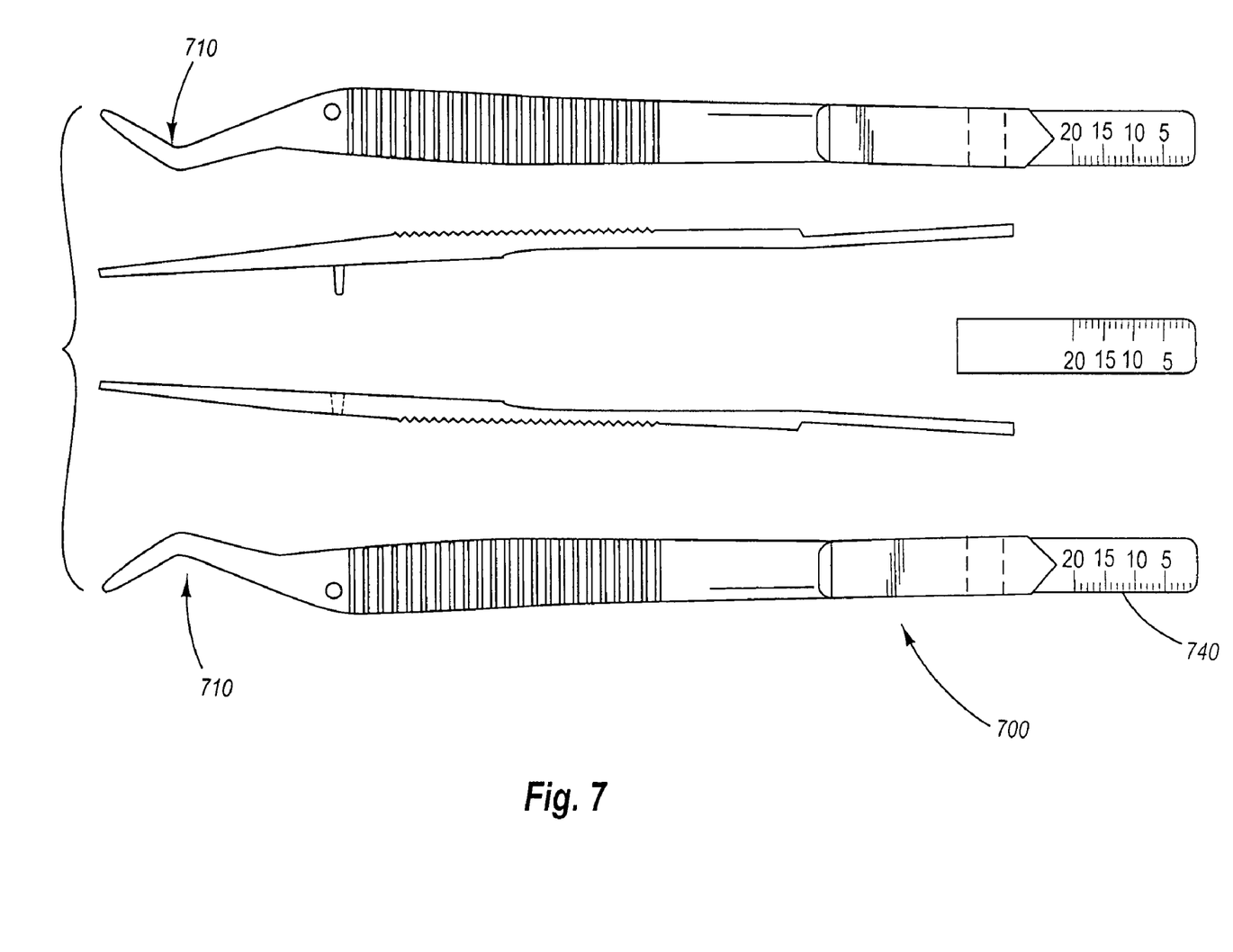
FIG. 7 is a variety of detailed plan views of a sixth tool of the present invention.

Referring now to FIG. 7, another tool of the instant invention is shown. This tool 700 is similar to many of the other tools that are shown in FIG. 1, such as the tool identified as tool 200. However, this tool 700 differs from the tool 200 in that the tool 700 has a more traditionally configured beak portion 710. This tool also contains a ruled measuring portion 740, which can be utilized to assist in properly placing and presenting items within the mouth of a patient, as well as for performing other measuring functions.

Figure 8:
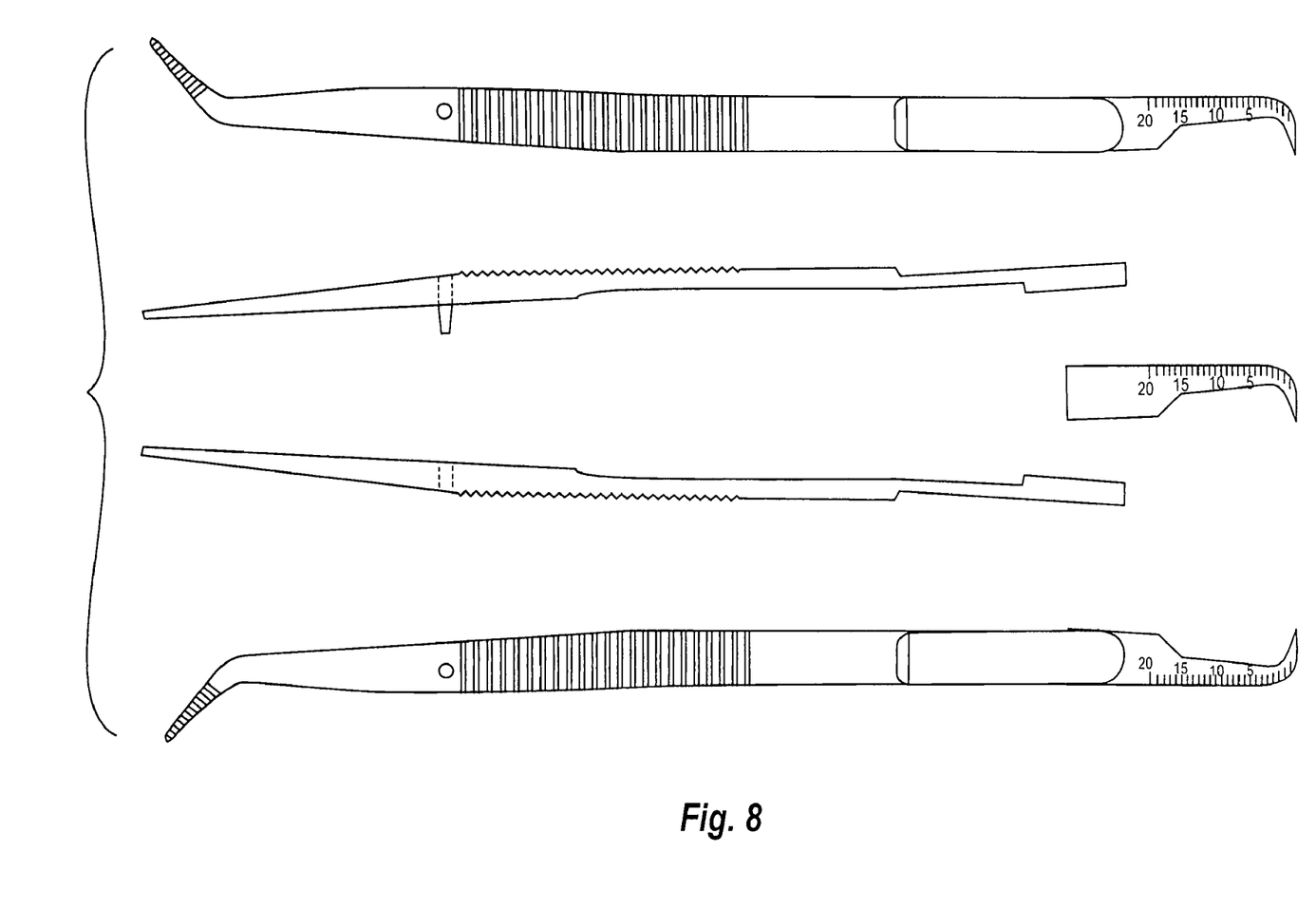
FIG. 8 is a variety of detailed plan views of a seventh tool of the present invention.

FIG. 8 shows another pliers tool 800. This pliers tool has a measured and calibrated beak which contains markings. This device also contains a curved tail portion that likewise contains measuring markings. The measuring markings allow a user to adapt and modify the position and location of various placements and to analyze and track the progress and locations of various portions of a patient's mouth. The hook end shown in this device further comprises a portion configured to fit within a 0.018 inch slot. Preferably, this is done by utilizing 27 gauge pieces of metal material to form the pieces of the tool shown in FIG. 8.

Figure 9:
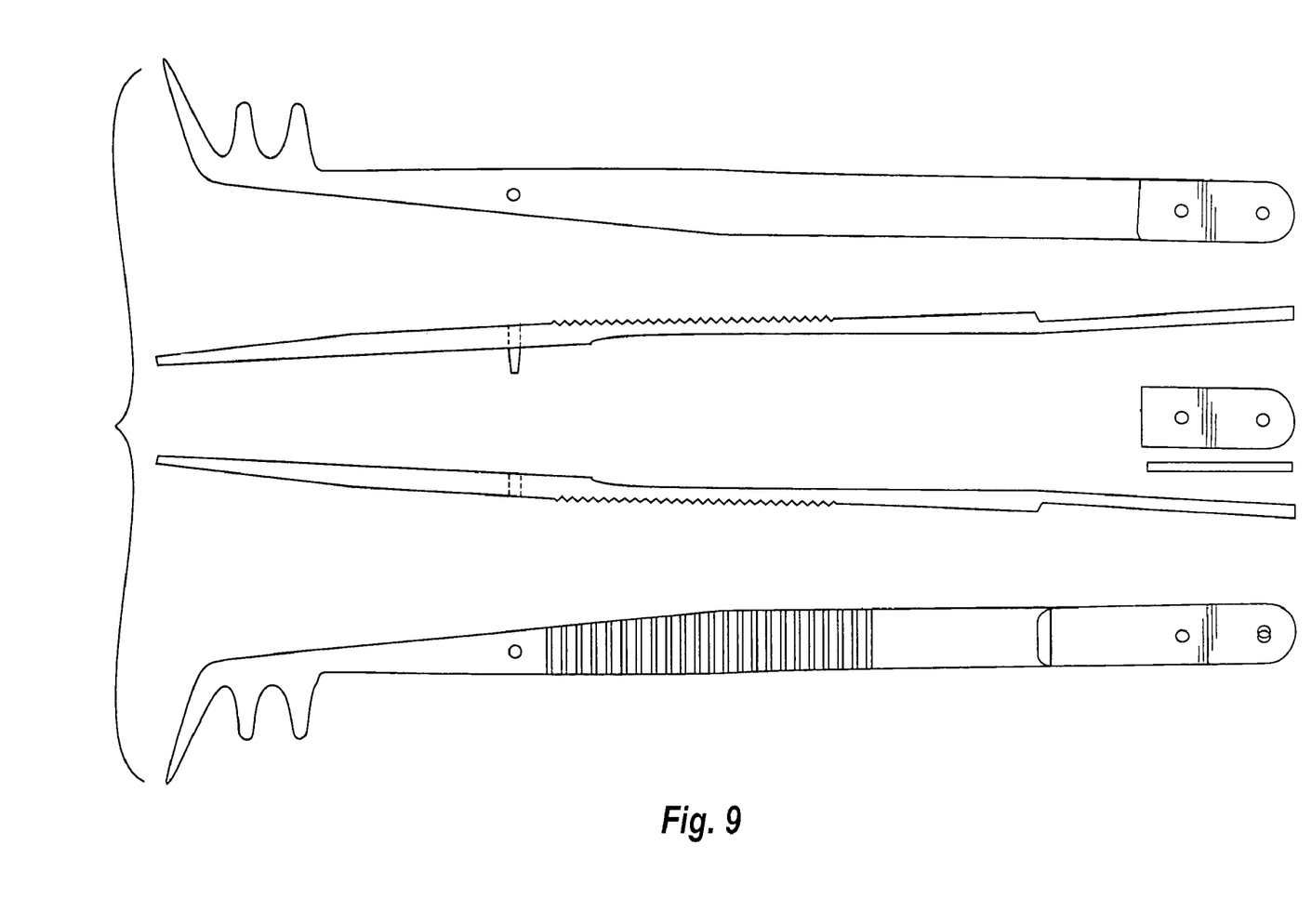
FIG. 9 is a variety of detailed plan views of an eighth tool of the present invention.

FIG. 9 shows a view of drawer tool pliers similar to the tool 600. This device is, however, made of a single piece of material.

Figure 10:
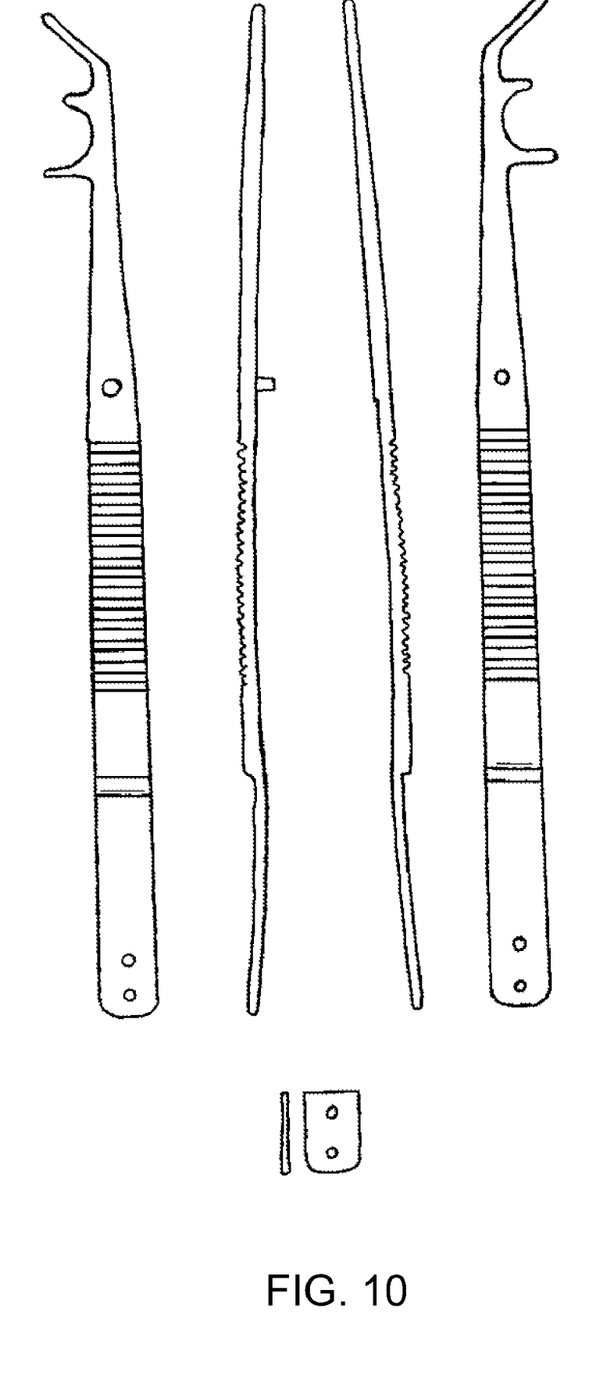
FIG. 10 is a variety of detailed plan views of a ninth tool of the present invention.

FIG. 10 shows a view of drawer tool pliers similar to the tool 600 and that shown in FIG. 9. This device, however, has a first drawer grasping portion, i.e., a first grasping finger, that is longer than the second drawer grasping portion, i.e., the second grasping finger.

While there is shown and described the present preferred embodiment of the invention, it is to be distinctly understood that this invention is not limited thereto but may be variously embodied to practice within the scope of the following claims. From the foregoing description, it will be apparent that various changes may be made without departing from the spirit and scope of the invention as defined by the following claims.

I claim:

1. An orthodontic tool for use in an orthodontist's office comprising:
    a pair of flat generally elongated arms placed in an adjacent lengthwise relationship, each arm having:
        a first end, wherein the first ends of both arms are connected together;
        a second end opposite the first, wherein the second ends of both arms are movable toward and away from one another;
        a central portion, extending from said first end;
        a tapering portion that tapers throughout its length, extending from said central portion to said second end;
        a drawer-grasping portion comprising a first grasping finger and a second grasping finger, said first and second grasping fingers extending essentially perpendicularly from said tapering portion, said first and second grasping fingers defining a semicircular notch generally perpendicularly disposed in relation to an axis formed between said first end and said second end, said notch adapted to engage a drawer handle therein;
    a curved portion, extending from said tapering portion at said second end; and
    a beak extending from said curved portion, said beak being disposed at a nonzero angle with regard to said axis of the arm and the first and second fingers, said beak extending to a tip that is spaced farther from said arm axis than the ends of said first and second grasping fingers, said beak being configured to not come into contact with said drawer handle while said drawer handle is being engaged by said notch and while the drawer is being opened and closed, the beaks of both arms being movable toward one another to grab items within the drawer once opened without said first or second grasping fingers coming into contact with said items within said drawer.

2. The tool of claim 1 wherein each of said beaks has a length of less than one inch.

3. The tool of claim 1 wherein each of said beaks is disposed in an obtuse angle adjacent said arms, such that said angle between said arm and said beak is greater than 90 degrees.

4. The tool of claim 1 wherein said orthodontic tool further comprises a measuring device.

5. The tool of claim 4 wherein said measuring device is a ruler attached to said first ends.

6. The tool of claim 4 wherein said measuring device is a scale etched within said outer beak's surface.

7. The tool of claim 1 wherein said notch is adapted to engage a wire-type drawer handle therein.

8. The orthodontic tool of claim 1, wherein said first grasping finger is located nearer to said first end than said second grasping finger and said first grasping finger extends farther away from said tapering member than said second grasping finger.

9. An orthodontic tool for use in an orthodontist's office comprising:
- a pair of flat generally elongated arms placed in an adjacent lengthwise relationship, each arm having
- a first end, wherein the first ends of both arms are connected together;
- a second end opposite the first, wherein the second ends of both arms are movable toward and away from one another;
- a central portion, extending from said first end;
- a tapering portion that tapers throughout its length, extending from said central portion to said second end;
- a curved portion, extending from said tapering portion at said second end;
- a drawer-grasping device attached along said arm, said drawer-grasping device comprising a first grasping finger and a second grasping finger, said first and second grasping fingers extending essentially perpendicularly from said arm; said first and second grasping fingers defining a semicircular notch generally perpendicularly disposed in relation to an axis formed between said first and second ends; said notch adapted to engage a wire-type drawer handle therein; and
- a beak extending from said curved portion, said beak being disposed at a nonzero angle with regard to said axis of the arm and the first and second fingers, said beak extending to a tip that is spaced farther from said arm axis than the ends of said first and second grasping fingers, said beak being configured to not come into contact with said drawer handle while said drawer handle is being engaged by said notch and while the drawer is being opened and closed, the beaks of both arms being moveable toward one another to grab items within the drawer once opened without said first or second grasping fingers coming into contact with said items within said drawer.

10. The orthodontic tool of claim 9, wherein said first grasping finger is located nearer to said first end than said second grasping finger and said first grasping finger extends farther away from said arm than said second grasping finger.

11. A set of orthodontic tools for use in an orthodontists office comprising:
- a first tool comprised of a pair of flat generally elongated arms placed in an adjacent lengthwise relationship, each arm having a first end extending to a central portion said central portion extending to a tapering member that tapers throughout its length, said tapering member extending to a curve portion and said curve portion extending to a beak at a second end, said beak being acutely angularly disposed with regard to said arms and having an inner surface, an outer surface, and length of less than one inch, said beaks dimensioned so as to grasp a base portion of an orthodontic bracket having wings beneath said wings for placement upon a tooth and to grasp an orthodontic bracket having a wire slot within said wire slot, said arms being connected at said first ends and configured to push said central portions, tapering members, curve portions and said beak inner surfaces apart;
- a second tool comprised of a pair of flat generally elongated arms placed in an adjacent lengthwise relationship, each arm having a first end extending to a central portion said central portion extending to a tapering member that tapers throughout its length, said tapering member extending to a curve portion and said curve portion extending to a beak at a second end, said beak being angularly disposed with regard to said arms and having an inner surface and an outer surface, said inner surface connected to a generally flat round plate, said plate adapted to grasp an orthodontic bracket having wings beneath said wings and to grasp an orthodontic bracket having a wire channel within said wire channel for placement of said bracket upon a tooth, said arms being connected at said first ends and configured to push said central portions, tapering members, curve portions and said beak inner surfaces apart;
- a third tool comprised of a pair of flat generally elongated arms placed in an adjacent lengthwise relationship, each arm having a first end extending to a central portion said central portion extending to a tapering member that tapers throughout its length, said tapering member extending to a first curved portion and said first curved portion extending to a second curved portion said second curved portion extending to a beak at a second end, said beak being angularly disposed with regard to said arms and having an inner surface, an outer surface and a length of less than one inch, said beaks dimensioned so as to grasp a base portion of an orthodontic brace having wings beneath said wings, and to grasp an orthodontic brace having a wire channel within said wire channel for placement upon a tooth, said arms being connected at said first ends and configured to push said central portions, tapering members, curve portions and said beak inner surfaces apart;
- a fourth tool comprised of a pair of flat generally elongated arms placed in an adjacent lengthwise relationship, each arm having a first end extending to a central portion said central portion extending to a tapering member that tapers throughout its length, said tapering member extending to a first curved portion and said first curved portion extending to a second curved portion said second curved portion extending to a beak at a second end, said beak being angularly disposed with regard to said arms and having an inner surface, an outer surface and a length of less than one inch, said inner surface having a generally flat round plate attached thereto dimensioned so as to grasp a base portion of an orthodontic brace having wings beneath said wings, and to grasp an orthodontic brace having a wire channel within said wire channel for placement upon a tooth, said arms being connected at said first ends and configured to push said central portions, tapering members, curve portions and said beak inner surfaces apart;
- a fifth tool comprising
  - a pair of flat generally elongated arms placed in an adjacent lengthwise relationship, each arm having:
    - a first end, wherein the first ends of both arms are connected together;
    - a central portion extending from said first end;
    - a tapering portion that tapers throughout its length, extending from said central portion to said second end;

a drawer-grasping portion comprising a first grasping finger and a second grasping finger, said first and second grasping fingers extending essentially perpendicularly from said tapering portion, said first and second grasping fingers defining a semicircular notch generally perpendicularly disposed in relation to an axis formed between said first end and said second end, said notch adapted to engage a drawer handle therein;

a curve portion extending from said tapering portion at said second end; and a beak, extending from said curved portion, said beak being disposed at a nonzero angle with regard to said axis of the arm and the first and second fingers, said beak extending to a tip that is spaced farther from said arm axis than the ends of said first and second grasping fingers, said beak being configured to not come into contact with said drawer handle while said drawer handle is being engaged by said notch and while the drawer is being opened and closed, the beaks of both arms being movable toward one another to grab items within the drawer once opened without said first or second grasping fingers coming into contact with said items within said drawer ; and a sixth tool comprised of a pair of flat generally elongated arms placed in an adjacent lengthwise relationship, each arm having a first end extending to a central portion said central portion extending to a tapering member that tapers throughout its length, said tapering member extending to a curve portion and said curve portion extending to a beak at a second end, said beak being angularly disposed with regard to said arms and having an inner surface and an outer surface, said arms being connected at said first ends and configured to push said central portions, tapering members, curve portions and said beak inner surfaces apart, said first ends further comprising a ruler attached to said first ends, and said outer surface having a measuring scale etched within.

* * * * *